US005786516A

United States Patent [19]
Maliverney

[11] Patent Number: 5,786,516
[45] Date of Patent: *Jul. 28, 1998

[54] PROCESS FOR THE PREPARATION OF ISOVANILLIN

[75] Inventor: Christian Maliverney, Lyons, France

[73] Assignee: Rhone-Poulenc Chimie, Courbevoie, France

[*] Notice: The term of this patent shall not extend beyond the expiration date of Pat. No. 5,648,552.

[21] Appl. No.: 800,818

[22] Filed: Feb. 14, 1997

Related U.S. Application Data

[63] Continuation of Ser. No. 546,648, Oct. 23, 1995, Pat. No. 5,648,552.

[30] Foreign Application Priority Data

Oct. 24, 1994 [FR] France .................................. 94 12661

[51] Int. Cl.$^6$ .............................................. C07C 45/65
[52] U.S. Cl. ..................................................... 568/433
[58] Field of Search ......................................... 568/433

[56] References Cited

U.S. PATENT DOCUMENTS

| | | | |
|---|---|---|---|
| 3,007,978 | 7/1961 | Alt | 568/433 |
| 3,367,972 | 2/1968 | Gitchel et al. | 568/433 |
| 4,065,504 | 12/1977 | Findlay | 568/433 |
| 4,453,004 | 6/1984 | Nelson | 568/433 |
| 4,453,017 | 6/1984 | Nelson | 568/433 |
| 4,473,713 | 9/1984 | Ratton | 568/433 |
| 4,487,975 | 12/1984 | Ratton | 568/433 |

*Primary Examiner*—James H. Reamer
*Attorney, Agent, or Firm*—Craig M. Bell

[57] ABSTRACT

The present invention relates to a novel process for the preparation of isovanillin.

The process for the preparation of isovanillin according to the invention is characterized in that it consists in dealkylation being carried out using a strong acid, selectively in the 3-position, on a 3-alkoxy-4-methoxybenzaldehyde wherein said alkoxy group has at least two carbon atoms.

28 Claims, No Drawings

PROCESS FOR THE PREPARATION OF ISOVANILLIN

This application is a continuation of U.S. Ser. No. 08/546,648 filed on Oct. 23, 1995 now U.S. Pat. No. 5,648,552.

The present invention relates to a novel process for the preparation of isovanillin.

Isovanillin, or 3-hydroxy-4-methoxybenzaldehyde, is a synthesis intermediate which is used in particular in the pharmaceutical, cosmetics, agrochemical and food fields.

Several routes of access are described in the prior art, and there may in particular be mentioned processes which consist in starting with piperonal (or 3,4-(methylenedioxy) benzaldehyde) and in reacting it with sodium methoxide, in the presence of cuprous chloride, in an organic solvent, namely dimethylformamide [Baratov et al., Zh. Org. Khim., 27, (7), 1578 (1991)]. The main drawbacks of this process are the cost of the starting material used and the drawbacks associated with the use of an organic solvent which must be recovered in order to recycle it.

Isovanillin may also be prepared from veratraldehyde (or 3,4-dimethoxybenzaldehyde) by carrying out a selective demethylation using methionine in methanesulphonic acid [Fujii et al., J. Chem. Soc. Perkin Trans. 1, 20, 2288 (1977)]. The process is long, methanesulphonic acid is expensive and the selectivity for isovanillin is not very good.

Kessar et al. [J. Chem. Soc. Chem. Commun., 7, 400 (1983)], also describe a process for obtaining isovanillin by selective 0-methylation of protocatechualdehyde (or 3,4-dihyroxybenzaldehyde) by methyl iodide, in the presence of sodium hydride and in dimethyl sulphoxide. The isovanillin yield obtained is only 65 %. This synthetic route also suffers from not being economically competitive, since the starting material is not an industrial product and the presence of the organic solvent increases the production cost.

Another process, which is also expensive, described by Scarpati et al., [Synth. Commun., 20, (17), 2565 (1990)] consists of the formylation of guaiacol protected in the form of the acetate, by dichloromethoxymethane, in the presence of titanium tetrachloride in dichloromethane, which leads to 3-acetoxy-4-methoxybenzaldehyde which is then hydrolysed using sodium hydroxide. Besides the large number of steps, this process uses dichloromethoxymethane which is an expensive and toxic product, and also involves an organic solvent.

Moreover, U.S. Pat. No. 3,367,972 describes a process for the preparation of isovanillin by acid hydrolysis of veratraldehyde. However, the reaction is slow and not very selective. In Example 1, the degree of conversion of the aldehyde is only 35.8% after 360 min at 70.5–72.3° C., and the isovanillin obtained (33.2%) is accompanied by vanillin (2.9%) which must be separated out.

None of these processes is satisfactory since they are difficult to transfer to the industrial scale, either on account of poor reaction yields or for economic reasons.

The subject of the present invention is to provide an improved process which makes it possible to circumvent the abovementioned drawbacks.

It has now been found that isovanillin can be prepared, in a rapid reaction and with a very good reaction yield, according to a process which consists in carrying out the dealkylation using a strong acid, selectively in the 3-position, of a 3-alkoxy-4-methoxybenzaldehyde wherein said alkoxy group has at least two carbon atoms.

Indeed, it has been demonstrated that isovanillin can be prepared under advantageous economic conditions insofar as the dealkylation is carried out on a 3-alkoxy-4-methoxybenzaldehyde whose leaving alkoxy group has a carbon condensation higher than the methoxy group.

According to a preferred embodiment of the invention, the 3-alkoxy-4-methoxybenzaldehyde is prepared by 0-methylating a 3-alkoxy-4-hydroxybenzaldehyde having an alkoxy group which has at least two carbon atoms.

Thus, in its preferred form, the process for the preparation of isovanillin, according to the invention, comprises:
a first step, in which 0-methylation is carried out on a 3-alkoxy-4-hydroxybenzaldehyde having an alkoxy group which has at least two carbon atoms, and a second step, in which the 3-alkoxy-4-methoxybenzaldehyde obtained is selectively dealkylated in the 3-position, with a strong acid, thereby allowing isovanillin to be obtained.

In accordance with the process of the invention, the starting material used is 3-alkoxy-4-methoxybenzaldehyde corresponding more particularly to the following formula (I):

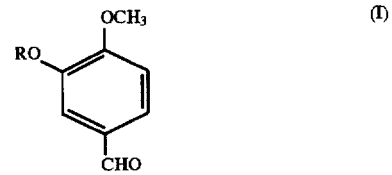

in the said formula (I), R represents an alkyl or cycloalkyl radical having at least 2 carbon atoms.

The invention preferably involves a 3-alkoxy-4-methoxybenzaldehyde of formula (I) in which the radical R is preferably an alkyl or cycloalkyl radical having a number of carbon atoms which ranges between 2 and 8.

Although, from a chemical point of view, the nature of the radical chosen is of little importance as long as it comprises at least two carbon atoms, it should be noted that from an economic point of view it is preferable to select the radical R from the ethyl, propyl, isopropyl, n-butyl, isobutyl, sec-butyl and tert-butyl radicals.

Among the substrates of formula (I) most particularly used are 3-ethoxy-4-methoxybenzaldehyde, 3-n-propoxy-4-methoxybenzaldehyde, 3-isopropoxy-4-methoxybenzaldehyde, 3-n-butoxy-4-methoxybenzaldehyde, 3-isobutoxy-4-methoxybenzaldehyde, 3-sec-butoxy-4-methoxybenzaldehyde and 3-tert-butoxy-4-methoxybenzaldehyde.

In accordance with the process of the invention, the 3-alkoxy-4-methoxybenzaldehyde is reacted with a strong acid.

Several mandatory conditions govern the choice of the organic solvent. A first characteristic feature of this acid is that it is a strong acid. The term strong acid denotes an acid having a pKa in water of less than 3.

The lower limit is not of essential nature.

The pKa is defined as the ionic dissociation constant of the acid/base pair when water is used as solvent.

A second characteristic feature of this acid is that it is a non-oxidizing acid under the reaction conditions. Thus, acids such as nitric acid are therefore excluded from the invention.

As examples of acids which are particularly suitable for carrying out the process of the invention, there may be mentioned halogenated acids such as hydrochloric acid, hydrobromic acid and hydriodic acid.

It is also possible to use halogenated or non-halogenated oxyacids such as sulphuric acid, pyrosulphuric acid; halogenated or non-halogenated sulphonic acids such as fluorosulphonic acid, chlorosulphonic acid, trifluoromethanesulphonic acid, methanesulphonic acid, ethanesulphonic acid, ethanedisulphonic acid, benzenesulphonic acid, benzenedisulphonic acids, toluenesulphonic acids, naphthalenesulphonic acids and naphthalenedisulphonic acids.

Among these acids, hydrochloric acid, hydrobromic acid and sulphuric acid will preferably be used.

Sulphuric acid is preferably chosen.

The concentration of the starting strong acid may vary according to commercial availability.

For example, if hydrochloric acid or hydrobromic acid is used, the concentration of the acid ranges between 30 and 50% by weight.

If sulphuric acid is used, its concentration advantageously ranges between 80 and 100% by weight, preferably between 90 and 99% by weight. According to a preferred embodiment of the invention, a sulphuric acid solution which is as concentrated as possible is used: this concentration is between 95 and 99% by weight.

The ratio between the number of moles of strong acid used and the number of moles of 3-alkoxy-4- methoxybenzaldehyde may vary widely, for example between 2 and 80.

It is preferable for the said molar ratio to be between 3 and 15 and even more preferably between 4 and 10.

The temperature at which the process of the invention is performed may vary widely, for example between 0° C. and 150° C.

From an economic point of view, it is advantageous not to heat the reaction medium. However, heating may prove to be necessary in certain cases.

The temperature selected depends on the nature of the acid used and on the nature of the group R to be removed.

It has been found that the larger and more branched the group R to be removed, the lower it is possible for the reaction temperature selected to be.

The appropriate reaction temperature to use may readily be determined by those skilled in the art by performing simple operations.

Thus, examples illustrating the range of temperatures selected are given below.

When sulphuric acid is used, the temperature generally ranges between 0° C. and 100° C.

When the group R to be removed is a linear alkyl group such as, for example, ethyl, n-propyl or n-butyl, the reaction temperature chosen is advantageously between 50 and 90° C., preferably between 60° C. and 80° C.

When R is a branched alkyl group, that is to say a group in which the carbon atom located in the α -position relative to the oxygen atom is at least secondary, that is to say an isopropyl, sec-butyl or tert-butyl group, the reaction temperature is preferably between 0° C. and 40° C., and even more preferably between 0° C. and 30° C.

If a halogenated acid such as hydrochloric acid or hydrobromic acid is used, the reaction temperature selected, in the case of a linear alkyl group R, is preferably between 100 and 150° C., and even more preferably between 100° C. and 130° C.

If the group R is a branched alkyl group, the reaction temperature chosen is then advantageously between 50 and 100° C., preferably between 60 and 80° C.

From a practical point of view, the process of the invention is easy to carry out since it does not require the use of specific apparatus.

In practice, the process of the invention may be carried out in the manner described below.

The various constituents of the reaction mixture are loaded into the chosen equipment. In a preferred manner, the strong acid is introduced into the 3-alkoxy-4-methoxybenzaldehyde, but it is also possible to carry out the inverse operation. Thus, the molten 3-alkoxy-4-methoxybenzaldehyde may be introduced into the strong acid or the substrate may be added in suspension in the strong acid.

It is preferable to perform the process of the invention under an atmosphere of dry gases. An atmosphere of rare gases, preferably argon, may be established, but nitrogen is preferred.

Once the atmosphere of dry gas has been established, the reaction mixture is brought to the chosen temperature, optionally by heating.

The duration of the reaction may vary widely. It is dependent on the nature of the 3-alkoxy-4-methoxybenzaldehyde, the strong acid and the concentration thereof, and the temperature.

Under the preferred conditions of the invention, which are the use of a concentrated strong acid, the duration of the reaction varies, for example, from 30 minutes to 6 hours, according to the temperature at which the reaction is carried out.

At the end of the reaction, the reaction mass is returned to room temperature. The term room temperature generally refers to a temperature of between 18° C. and 25° C.

In certain cases, it may turn out to be necessary to cool to a temperature of between 10° C. and 15° C.

One embodiment which makes it possible to separate the desired product from the reaction mass is given below, by way of illustration.

Generally, on account of the presence of the concentrated strong acid, the reaction mass is diluted with water or with ice such that the concentration of strong acid is from 20 to 30% by weight.

The isovanillin formed is extracted with a water-insoluble organic solvent, and there may in particular be mentioned ether oxides, preferably ethyl ether or isopropyl ether; chlorinated hydrocarbons, preferably chloroform or dichloroethane; water-insoluble ketones, preferably methyl isobutyl ketone.

Methyl isobutyl ketone is preferably selected.

The organic and aqueous phases are separated.

The aqueous phase contains the strong acid, which may be regenerated and recycled.

The organic phase is washed with water and a basic agent is then added such that the pH is between 6.5 and 7.0.

Aqueous sodium hydroxide solution is preferably used.

The organic solvent is evaporated off. The isovanillin precipitates. It is isolated according to the standard techniques of solid/liquid separation, preferably by filtration.

The solid obtained may be purified, in particular by crystallization.

According to a preferred embodiment of the invention, the 3-alkoxy-4-methoxybenzaldehyde is prepared by O-methylating a 3-alkoxy-4- hydroxybenzaldehyde having an alkoxy group which has at least two carbon atoms.

In accordance with a preferred embodiment of the process of the invention, the starting material used is a 3-alkoxy-4-hydroxybenzaldehyde corresponding more particularly to the following formula (II):

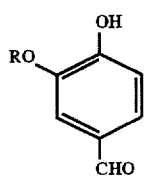

(II)

in the said formula (II), R represents an alkyl or cycloalkyl radical having at least 2 carbon atoms.

The invention preferably involves a 3-alkoxy-4-hydroxybenzaldehyde of formula (II) in which the radical R is preferably an alkyl or cycloalkyl radical having a number of carbon atoms which may range between 2 and 8.

Among the substrates of formula (II) most particularly used are 3-ethoxy-4-hydroxybenzaldehyde, 3-n-propoxy-4-hydroxybenzaldehyde, 3-isopropoxy-4-hydroxybenzaldehyde, 3-n-butoxy-4-hydroxybenzaldehyde, 3-isobutoxy-4-hydroxybenzaldehyde, 3-sec-butoxy-4-hydroxybenzaldehyde and 3-tert-butoxy-4-hydroxybenzaldehyde.

When 3-ethoxy-4-hydroxybenzaldehyde, which is a commercially available product, is used, the process of the invention is very competitive with respect to the processes described.

According to the invention, the 3-alkoxy-4-hydroxybenzaldehyde is 0-methylated by reacting it with a methylating agent.

Various types of alkylating agent may be used, and there may more particularly be mentioned methyl halides, preferably methyl chloride or methyl bromide, dimethyl sulphate, methyl p-toluenesulphonate and methyl methanesulphonate.

Among the abovementioned alkylating agents, methyl chloride and dimethyl sulphate are preferred.

Generally, the 0-methylation reaction is advantageously performed at a pH of between 8 and 10 and, preferably, above 9.

The abovementioned pH may be obtained, if necessary, by addition of a base, preferably an aqueous solution of an alkali metal hydroxide or of an alkali metal hydrogen carbonate or carbonate. Any alkali metal hydrogen carbonate, carbonate or hydroxide may be used. The chosen concentration for the solution of the basic agent is advantageously high, preferably between 30 and 60% by weight.

However, for economic considerations, sodium hydroxide is preferred and commercial solutions of sodium hydroxide having a concentration of 30% are more preferably used.

There is no disadvantage in using an organic base, but, from an economic point of view, sodium hydroxide is preferably selected.

As regards the amount of the reactants to use in this 0-alkylation step, the preferred amounts are defined below.

The concentration of the starting substrate, namely the 3-alkoxy-4-hydroxybenzaldehyde, in the reaction medium is advantageously between 10 and 25%.

The amount of alkylating agent employed depends on the amount of substrate to be alkoxylated. I t i s preferably at least equal to the stoichiometric amount and up to an excess which may be as high as 100%.

In other words, the alkylating agent/3-alkoxy-4-hydroxybenzaldehyde molar ratio ranges between 1.0 and 2.0 and, preferably, between 1.1 and 1.5.

As regards the reaction conditions, it is preferable to perform the process of the invention under an atmosphere of inert gas. An atmosphere of rare gases, preferably argon, may be established, but it is more economical to use nitrogen.

Once the atmosphere of inert gas has been established, the reaction mixture is brought to the chosen temperature The temperature of the 0-methylation reaction is not critical; it has an influence on the reaction kinetics. Generally, the 0-methylation reaction is performed at between 60° C. and 100° C. The reaction is preferably performed at a temperature of between 80° C. and 95° C.

The duration of the 0-methylation reaction depends in particular on the reaction temperature. It usually ranges between 1 hour and 8 hours. A duration of from 1 to 4 hours is generally sufficient.

According to a practical embodiment of the invention, it is possible firstly to introduce the 3-alkoxy-4-hydroxybenzaldehyde, the basic solution, to bring the mixture to the reaction temperature and then to add the alkylating agent and optionally the base if this is required in order to adjust the pH to within the abovementioned region.

At the end of the reaction, after cooling, an organic phase comprising the 3-alkoxy-4- methoxybenzaldehyde is recovered.

It is possible to employ the organic phase, without any separation, in the dealkylation step after having preferably removed the water.

It is also possible to separate out the 3-alkoxy-4-methoxybenzaldehyde, according to the standard separation techniques.

It is possible in particular to separate it by extraction into a suitable, water-insoluble solvent. The solvents mentioned above are suitable for use, but methyl isobutyl ketone is preferably selected.

The 3-alkoxy-4-methoxybenzaldehyde obtained may optionally be purified in a standard manner, by distillation or by crystallization.

It may then be employed in the dealkylation step, according to the process of the invention.

The process of the invention makes it possible to obtain isovanillin selectively.

The examples which follow illustrate the invention without, however, limiting the scope thereof.

EXAMPLES

In the examples, the abbreviations have the following meanings:

EVA = ethyl vanillin = 3-ethoxy-4- hydroxybenzaldehyde,
EMBA = 3-ethoxy-4-methoxybenzaldehyde, $$\text{Yield} = \frac{\text{number of moles of isovanillin formed}}{\text{number of moles of } EMBA \text{ employed}} \%$$

Example 1

Methylation of ethyl vanillin with dimethyl sulphate

After a nitrogen atmosphere has been established, 332.4 g of ethyl vanillin are loaded into a 2000 ml 3-necked round-bottomed flask heated by an electric heating mantle, stirred mechanically, and equipped with two dropping funnels, a condenser, devices for measuring the temperature and the pH, and a nitrogen inlet.

0.5 liter of water is added and the mixture is heated to 90° C.

360 g of aqueous 30.5% sodium hydroxide solution (pH=9) are added, followed by 350 g of dimethyl sulphate, over 2 hours.

The reaction medium is left stirring for 1 hour at 90° C. and is then cooled to 70° C. and allowed to separate by settling.

The upper organic layer is washed and is then distilled at 120° C. under a reduced pressure of 10 mm of mercury (1330 pa), to give 3-ethoxy-4-methoxybenzaldehyde.

The results obtained, after assaying by high performance liquid chromatography, are as follows:

Yield before distillation: 98.4% purity before distillation: 97% (3% water)

purity after distillation: 99.9%

De-ethylation of 3-ethoxy-4-methoxybenzaldehyde with sulphuric acid

After having established an atmosphere of inert gas, 270.5 g of 3-ethoxy-4-methoxybenzaldehyde and 742 g of 98 % sulphuric acid are loaded into a 1.5 liter jacketed reactor equipped with a mechanical stirrer, a thermometer and a nitrogen input.

The mixture is heated for 3 hours 30 minutes at 65° C.

The assay by high performance liquid chromatography gives:

Conversion of the EMBA=98.5%

Yield of isovanillin=96%

The reaction mass is cooled and run into 2 liters of ice-cold water, with stirring.

The precipitate which forms is dissolved with 2 liters of methyl isobutyl ketone.

The organic phase is separated out; the aqueous phase is reextracted with 0.75 liter of methyl isobutyl ketone. The mother liquors (30% $H_2SO_4$) may be generated.

The organic phase is washed to pH=7 and is en evaporated at 60° C. under a reduced pressure of out 100 mm of mercury (13300 pa), to give isovanillin 14 g) in a purity equal to 95%.

I claim:

1. A process for the preparation of isovanillin, comprising carrying out a dealkylation, selectively in the 3-position of a 3-alkoxy-4-methoxybenzaldehyde using a strong acid wherein said alkoxy group has at least two carbon atoms.

2. The process according to claim 1 wherein the 3-alkoxy-4 methoxybenzaldehyde corresponds to the following formula (I):

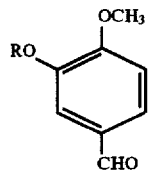

wherein R represents an alkyl or cycloalkyl radical having at least 2 carbon atoms.

3. The process according to claim 2, wherein R is an alkyl or cycloalkyl radical having a number of carbon atoms which ranges between 2 and 8, inclusive.

4. The process according to claim 1, wherein the 3-alkoxy-4-methoxybenzaldehyde is 3-ethoxy-4-methoxybenzaldehyde, 3-n-propoxy-4-methoxybenzaldehyde, 3-isopropoxy-4-methoxybenzaldehyde, 3-n-butoxy-4-methoxybenzaldehyde, 3-isobutoxy-4-methoxybenzaldehyde, 3-sec-butoxy-4-methoxybenzaldehyde and 3-tert-butoxy-4-methoxybenzaldehyde.

5. The process according to claim 1, wherein the acid has a pKa of less than or equal to 3.0.

6. The process according to claim 5, wherein the acid is selected from the group consisting essentially of halogenated acids, halogenated or non-halogenated oxyacids, halogenated or non-halogenated sulphonic acids and mixtures thereof.

7. The process according to claim 6, wherein the acid is selected from the group consisting essentially of hydrochloric acid, hydrobromic acid, sulphuric acid and mixtures thereof.

8. The process according to claim 7, wherein the concentration of acid ranges between about 30 and 50% by weight when the acid is hydrochloric acid or hydrobromic acid.

9. The process according to claim 7, wherein the concentration of acid ranges between about 80 and 100% by weight, when the acid is sulphuric acid.

10. The process according to claim 1, wherein the ratio between the number of moles of acid and the number of moles of 3-alkoxy-4-methoxybenzaldehyde ranges between about 2 and 80.

11. The process according to claim 1, wherein the reaction temperature ranges between about 0° C. and 150° C.

12. The process according to claim 11, wherein the reaction temperature ranges between about 50 and 90° C. when sulphuric acid is used.

13. The process according to claim 11 wherein the reaction temperature ranges between about 100° C. and 150° C. when hydrochloric acid or hydrobromic acid is used.

14. The process according to claim 1, wherein the acid is mixed as a solution into the 3-alkoxy-4-methoxybenzaldehyde.

15. The process according to claim 1, wherein the 3-alkoxy-4-methoxybenzaldehyde is prepared by 0-methylating a 3-alkoxy-4-hydroxybenzaldehyde having an alkoxy group which has at least two carbon atoms.

16. The process according to claim 15, wherein the 3-alkoxy-4-hydroxybenzaldehyde corresponds to the following formula (II):

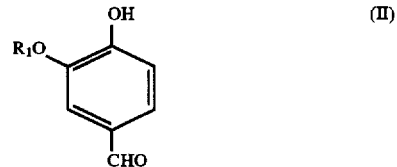

wherein $R_1$ represents an alkyl or cycloalkyl radical having at least 2 carbon atoms.

17. The process according to claim 16, wherein R is an alkyl or cycloalkyl radical having a number of carbon atoms which ranges between 2 and 8, inclusive.

18. The process according to claim 17, wherein the 3-alkoxy-4-hydroxybenzaldehyde can be 3-ethoxy-4-hydroxybenzaldehyde, 3-n-propoxy-4-hydroxybenzaldehyde, 3-isopropoxy-4-hydroxybenzaldehyde, 3-n-butoxy-4-hydroxybenzaldehyde, 3-isobutoxy-4-hydroxybenzaldehyde, 3-sec-butoxy-4-hydroxybenzaldehyde, and 3-tert-butoxy-4- hydroxybenzaldehyde.

19. The process according to claim 15, wherein the alkylating agent is a methylhalide.

20. The process according to claim 15, wherein the 0-methylation reaction is carried out at a pH of between about 8.0 and 10.0.

21. The process of claim 20 wherein said pH is maintained through the addition of an aqueous solution of an alkali metal hydrogen carbonate, alkali metal carbonate or alkali metal hydroxide.

22. The process according to claim 15, wherein the molar ratio of alkylating agent to 3-alkoxy-4- hydroxybenzaldehyde ranges between from about 1.0 to 2.0.

23. The process according to claim 15, wherein the temperature of the 0-methylation reaction is between about 60° C. and 1 00° C.

24. The process according to claim 23, wherein the 3-alkoxy-4-hydroxybenzaldehyde and the acidic solution are first mixed and the mixture is then heated to the reaction temperature, followed by the addition of the alkylating agent and the base, if required.

25. The process of claim 24 wherein said reaction yields an organic phase comprising 3-alkoxy-4-methoxybenzaldehyde which is subsequently recovered and isolated therefrom.

26. The process of claim 1 characterized in that the dealkylation reaction is carried out under an atmosphere of an inert gas.

27. The process of claim 15 characterized in that the O-methylation reaction is carried out under an atmosphere of an inert gas.

28. The process according to claim 6, wherein the acid is selected from the group consisting essentially of hydrochloric acid, hydrobromic acid, hydroiodic acid, sulphuric acid, pyrosulphuric acid, perchloric acid, fluorosulphonic acid, chlorosulphonic acid, trifluoromethanesulphonic acid, methanesulphonic acid, ethanesulphonic acid, ethanedisulphonic acid, benzenesulphonic acid, benzenedisulphonic acid, toluene sulphonic acids, naphthalenesulphonic acids, naphthalenedisulphonic acids and mixtures thereof.

* * * * *